United States Statutory Invention Registration [19]

[11] Reg. Number: H719

Collignon et al. [43] Published: Dec. 5, 1989

[54] PREPARATION OF SPHEROIDAL 3-NITRO-1,2,4-TRIAZOL-5-ONE BY CRYSTALLIZATION

[75] Inventors: Steven L. Collignon, Waldorf; Robert Farncomb, Accokeek, both of Md.

[73] Assignee: The United States of America as represented by the Secretary of the Navy, Washington, D.C.

[21] Appl. No.: 379,035

[22] Filed: Jul. 12, 1989

[51] Int. Cl.[4] ..... C07D 249/12; C07D 249/16; C07D 403/00; C07D 487/00

[52] U.S. Cl. ..... 548/265; 548/263

*Primary Examiner*—John F. Terapane
*Assistant Examiner*—John Covert
*Attorney, Agent, or Firm*—Kenneth E. Walden; Roger D. Johnson

[57] ABSTRACT

A process for recrystallizing crude, rod-like or jagged crystals of 3-nitro-1,2,4-triazol-5-one into spheroidal crystals by using water containing from 0.01 to 0.20 weight percent of a fluorochemical surfactant and from 0.01 to 0.20 weight percent of methyl cellulose.

4 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PREPARATION OF SPHEROIDAL 3-NITRO-1,2,4-TRIAZOL-5-ONE BY CRYSTALLIZATION

BACKGROUND OF THE INVENTION

This invention relates to heterocyclic organic explosives and more particularly to nitrated triazoles.

3-nitro-1,2,4-triazol-5-one (NTO) is typically recrystallized in ordinary water. Unfortunately, NTO recrystallizes from the water in jagged rod-like particles that have a tendency to agglomerate. The irregular and jagged crystal shapes causes the mixing of the formulations with NTO to be highly viscous and difficult to process and to pour. As a result, the amount of NTO which can be used in a processable explosive composition is limited and the performance of the explosive is therefore reduced.

S. L. Collignon in U.S. patent application, Ser. No. 07/213,037, filed on July 24, 1988, titled "Preparation of Spheroidal 3-Nitro-1,2,4-Triazol-5-One", discloses a method of manufacturing spheroidal NTO by recrystallizing NTO from alcohols of 1 to 4 carbon atoms or mixtures of these alcohols with water. The spheroidal NTO crystals produced were less than 150 microns in size. It would be desirable to provide a method by which larger spheroidal NTO crystals could be produced. Bimodal mixtures of large and small NTO crystals are ncessary to achieve high performance explosive mixtures. Also, explosives with high concentrations of NTO can be processed and poured into bombs using bimodal spheroidal NTO mixtures.

SUMMARY OF THE INVENTION

Accordingly an object of this inventio method of converting jagged rod-like 3-nitro-1,2,4-triazol-5-one crystals into spheroidal crystals.

Another object of this invention is to provide an inexpensive method of producing spheroidal crystals of 3-nitro-1,2,4-triazol-5-one.

A further object of this invention is to provide a method of producing spheroidal crystals of 3-nitro-1,2,4-triazol-5-one in the 300 to 500 micron range.

These and other objects of this invention are accomplished by providing:

a process comprising the following steps in order:

(1) completely dissolving 3-nitro-1,2,4-triazol-5-one in water containing from 0.01 to 0.20 weight percent of a fluorochemincal surfactant and from 0.01 to 0.20 weight percent of methyl cellulose at a temperature of from 60° C. to less than the boiling point of water at ambient pressure;

(2) cooling the aqueous solution formed in step (1) at a rate of from 6° C./minute to 20° C./minute while the solution is agitated until the solution is at a temperature of from 0° C. to 10° C.; and (3) isolating the product spheroidal crystals of 3-nitro1,2,4-triazol-5-one.

DETAILED DESCRIPTION OF THE PREFERRED EMBODIMENT

In this process, crude, jagged, rodlike 3-nitro-1,2,4-triazol-5-one are recrystallized in a water solution containing from 0.01 to 0.20, and more preferably from 0.05 to 0.10 weight percent of a fluorochemical surfactant and from 0.01 to 0.20 and preferably from 0.05 to 0.10 weight percent of methyl cellulose.

Surfactants are composed of an insoluble tail and a solubilizing group. In conventional hydrocarbon surfactants, the insoluble tail is usually a long hydrocarbon chain and the solubilizing group is a hydrophilic group such a sodium or potassium salt of a carboxylic or sulfonate group. In fluorochemical surfactants the hydrophobic hydrocarbon chain is replaced with a hydrophobic perfluoroalkyl or a fluorinated alkyl group. The solubilizing group will be hydrophilic.

The fluorochemical surfactants which can be used in this invention can be of the anionic, cationic, amphoteric, or nonionic type. Their hydrophobic tail can be a perfluoroakyl or a fluorinated alkyl chain. Types of surfactant which can be used include amine perfluoroalkyl sulfonates, ammonium perfluoroalkyl sulfonates, fluorinated alkyl quaternary ammonium iodides, fluorinated alkyl polyoxyethylene ethanols, and fluorinated alkyl amphoteric mixtures. The specific fluorochemical surfactants listed in Table 1 have been successfuly tested.

TABLE 1

| NAME[2] | TYPE | DESCRIPTION |
|---|---|---|
| Fluorad ® FC-99 | anionic | amine perfluoroalkyl sulfonates |
| Fluorad ® FC-100 | amphoteric | fluorinated alkyl amphoteric mixtures |
| Fluorad ® FC-120 | anionic | ammonium perfluoroalkyl sulfonates |
| Fluorad ® FC-135 | cationic | fluorinated alkyl quaternary ammonium iodides |
| Fluorad ® FC-170 | nonionic | fluorinated alkyl poly-oxyethylene ethanols |

[1]The information in the table is taken from a 3M product information booklet.
[2]Fluorad ® is a registered trademark of 3M.

In the first step of this process, crude, jagged, rod-like 3-nitro-1,2,4-triazol-5-one is dissolved in the surfactant-/water solution at a temperature of from 60° C. to just less than the boiling point of water at ambient pressure, and more preferably at 70° C. to 90° C. Care is taken to assure that all of the crude 3-nitro-1,2,4-triazol-5-one is dissolved. Even small amounts of crude rod-like 3-nitro-1,2,4-triazol-5-one can act as seed crystals causing formation of rod-like crystals rather than the desired spheroidal crystals. This is avoided by using less 3-nitro-1,2,4-triazol-5-one than the amount needed to form a saturated solution and by heating the solution for a sufficient time.

In the second step, the aqueous 3-nitro-1,2,4-triazole-5-one solution is cooled down to a temperature in the range of from 0° C. to 10° C. at a rate of from 6° C./minute to 20° C./minute. During the cool down, the solution is agitated (e.g., stirred) at a moderate to fast rate. As crystals are formed, the agitation causes them to collide with each other and with parts of the crystallizer (especially the agitator) thus breaking off new crystal nuolei. As is known in the art, this formation of secondary crystal nuclei helps the crystallization process.

Finally, the spheroidal 3-nitro-1,2-4-triazol-5-one crystals are collected (e.g., by filtration) and dried. The surfactant water filtrate can be reused in the process.

The general nature of the invention having been set forth, the following example is presented as a specific illustration thereof. It will be understood that the invention is not limited to this specific example but is susceptible to various modifications that will be recognized by one of ordinary skill in the art.

EXAMPLE

In a 2-liter flask, 80 g of 3-nitro-1,2,4-triazol-5-one, 0.8 g of Fluorad® FC-408 surfactant, and 0.8 g of methyl cellulose were added to 1 liter of water. This was heated at 80° C. until the 3-nitro-1,2,4-triazol-5-one had completely dissolved. With agitation (stirring), the solution was cooled with an ice bath to below 10° C. The product was separated by filtration and dried. The product was white spheroidal crystals of 3-nitro-1,2,4-triazol-5-one which were in the 300 to 500 micron size range.

The process was repeated successfully using Fluorad® FC-99 (amine perfluoroalkyl sulfonates), FC-100 (fluorinated alkyl amphoteric mixture), FC-120 (ammonium perfluoroalkyl sulfonates), FC-135 (fluorinated alkyl quaternary ammonium iodides), and FC-170-C (fluorinated alkyl polyoxyethelene ethanols). These include anionic, cationic, amphoteric, and nonionic types of surfactants. Fluorad® surfactants are available from the 3M Corporation, St. Paul, Minn.

Obviously, numerous modifications and variations of the present invention are possible in light of the above teachings. It is therefore to be understood that within the scope of the appended claims the invention may be practiced otherwise than as specifically described herein:

What is claimed is:

1. A process for producing spheroidal crystals of 3-nitro-1,2,4-triazol-5-one comprising the following steps in order:

(1) completely dissolving 3-nitro-1,2,4-triazol-5-one in water containing from 0.01 to 0.20 weight percent of a fluorochemincal surfactant and from 0.01 to 0.20 weight percent of methyl cellulose at a temperature of from 60° C. to less than the boiling point of water at ambient pressure;

(2) cooling the aqueous solution formed in step (1) at a rate of from 6° C./minute to 20° C./minute while the solution is agitated until the solution is at a temperature of from 0° C. to 10° C.; and (3) isolating the product spheroidal crystals of 3-nitro-1,2,4-triazol-5-one.

2. The process of claim 1 wherein the temperature range in step (1) is from 70° C. to 90° C.

3. The process of claim 1 wherein the water contains from 0.05 to 0.10 weight percent of the fluorochemical surfactant.

4. The process of claim 1 wherein the fluorochemical surfactant is selected from the group consisting of amine perfluoroalkyl sulfonates, ammonium perfluoroalkyl sulfonates, fluorinated alkyl quaternary ammonium iodides, fluorinated alkyl polyoxyethylene ethanols, and fluorinated alkyl amphoteric mixtures.

* * * * *